US008404657B2

(12) United States Patent
Liu et al.

(10) Patent No.: US 8,404,657 B2
(45) Date of Patent: Mar. 26, 2013

(54) MEANS AND METHODS FOR TREATING OR PREVENTING BRAIN TUMORS BASED ON THE NUCLEAR RECEPTOR TAILLESS (TLX)

(75) Inventors: Hai-Kun Liu, Heidelberg (DE); Günther Schütz, Heidelberg (DE)

(73) Assignee: DKFZ Deutsches Krebsforschungszentrum, Stiftung des Oeffentlichen Rechts, Heidelberg (DE)

( * ) Notice: Subject to any disclaimer, the term of this patent is extended or adjusted under 35 U.S.C. 154(b) by 42 days.

(21) Appl. No.: 12/744,802

(22) PCT Filed: Nov. 18, 2008

(86) PCT No.: PCT/EP2008/065731
§ 371 (c)(1),
(2), (4) Date: Oct. 25, 2010

(87) PCT Pub. No.: WO2009/068456
PCT Pub. Date: Jun. 4, 2009

(65) Prior Publication Data
US 2011/0038873 A1 Feb. 17, 2011

(30) Foreign Application Priority Data
Nov. 27, 2007 (EP) .................................. 07121641

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................... 514/44 A; 536/23.1; 536/24.1; 536/24.5; 435/375; 435/377

(58) Field of Classification Search .................. None
See application file for complete search history.

(56) References Cited

FOREIGN PATENT DOCUMENTS
WO  WO 99/32619 A1  7/1999
WO  WO 01/29058 A1  4/2001

OTHER PUBLICATIONS

Liu et al., Genes Dev. vol. 24:683-695, 2010.*
Vescovi et al., "Brain tumour stem cells", Nature Reviews Cancer, vol. 6 (2006), pp. 425-436.
Modena et al., "Identification of Tumor-Specific Molecular Signatures in Intracranial Ependymoma and Association With Clinical Characteristics", Journal of Clinical Oncology, vol. 24, No. 33 (2006), pp. 5223-5233.
Phillips et al., "Molecular subclasses of high-grade glioma predict prognosis, delineate a pattern of disease progression, and resemble stages in neurogenesis", Cancer Cell, vol. 9, No. 3 (2006), pp. 157-173.
Sharma et al., "Distinct Genetic Signatures among Pilocytic Astrocytomas Relate to Their Brain Region Origin", Cancer Research, vol. 67, No. 3 (2007), pp. 890-900.
Sim et al, "Neurocytoma Is a Tumor of Adult Neuronal Progenitor Cells", The Journal of Neuroscience, vol. 26, No. 48 (2006), pp. 12544-12555.
Taylor et al., "Radial glia cells are candidate stem cells of ependymoma", Cancer Cell, vol. 8 (2005), pp. 323-335.
Fire et al., "Potent and specific genetic interference by double-stranded RNA in *Caenorhabditis elegans*", Nature, vol. 391 (1998), pp. 806-811.
Fire, "RNA-triggered gene silencing", TIG, vol. 15, No. 9 (1999), pp. 358-363.
Kalota et al., "Progress in the Development of Nucleic Acid Therapeutics for Cancer", Cancer Biology & Therapy, vol. 3, No. 1, pp. 4-12 , Jan. 2004.
Zhu et al., "Understanding the Molecular Mechanism of Dominant Negative Action of Mutant Thyroid Hormone $\beta_1$-Receptors: The Important Role of the Wild-Type/Mutant Receptor Heterodimer", Endocrinology, vol. 137, No. 2 (1996), pp. 712-721.
Database EMBL [Online], "mtll=tailless homolog [mice, embryos, mRNA, 2026 nt]", XP-002466728, Sep. 27, 1995, Database accession No. S77482, 1 pg.
Liu et al., Expression of the nuclear receptor tailless is required for generation and maintenance of adult neural stem cells and participates in brain tumor generation, Cell Research, vol. 18, No. 43 (2008), 1 pg.
International Search Report, PCT/EP2008/065731, Feb. 10, 2009, 2 pgs.
International Preliminary Report on Patentability, PCT/EP2008/065731, Jun. 10, 2010, 6 pgs.
Galfre et al, "Preparation of Monoclonal Antibodies: Strategies and Procedures", Methods in Enzymology, vol. 73 (1981), 44 pgs.
Köhler et al., "Continuous cultures of fused cells secreting antibody of predefined specificity", Nature, vol. 256 (1975), pp. 495-497.
Smith et al., "Comparison of Biosequences", Advances in Applied Mathematics, vol. 2 (1981), pp. 482-489.
Needleman et al., "A General Method Applicable to the Search for Similarities in the Amino Acid Sequence of Two Proteins", J. Mol. Biol., vol. 48 (1970), pp. 443-453.
Monaghan et al., "The mouse homolog of the orphan nuclear receptor tailless is expressed in the developing forebrain", Development, Company of Biologists, vol. 121, No. 3 (1995), pp. 839-853.
Higgins et al., "Fast and sensitive multiple sequence alignments on a microcomputer", Cabios Communications, vol. 5, No. 2 (1989), pp. 151-153.
Feng et al., "Progressive Sequence Alignment as a Prerequisite to Correct Phylogenetic Trees", J. Mol. Evol., vol. 25 (1987), pp. 351-360.

* cited by examiner

*Primary Examiner* — Sean McGarry
(74) *Attorney, Agent, or Firm* — Fanelli Haag & Kilger PLLC

(57) ABSTRACT

The present invention relates to the use of an inhibitor of tailless gene expression or tailless protein activity for the preparation of a pharmaceutical composition for treating or preventing the brain tumor in a subject. Preferably an inhibitor of tailless expression is a single or double stranded RNA. An inhibitor of tailless protein activity is preferably an antibody which specifically binds thereto. Finally, the invention includes methods for identifying anti-brain tumor drugs.

4 Claims, 2 Drawing Sheets

Figure 1:
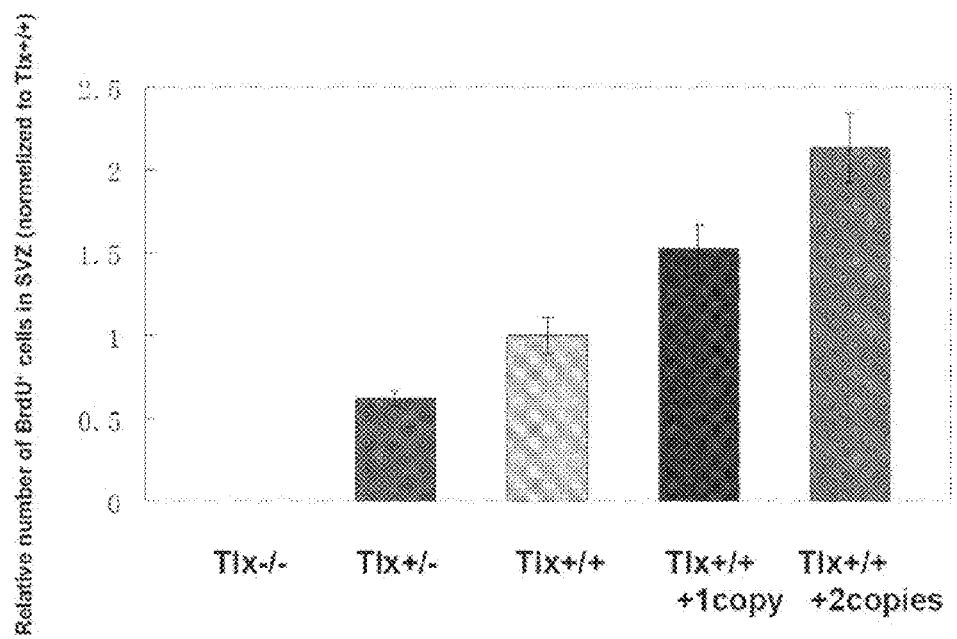

SEQUENCE LISTING

```
<160> NUMBER OF SEQ ID NOS: 6

<210> SEQ ID NO 1
<211> LENGTH: 3232
<212> TYPE: DNA
<213> ORGANISM: Homo sapiens

<400> SEQUENCE: 1
gcacaaagtc acagggtaat gaacttcggg gacccttcgc cgctgcgtgc gcggctgtcc      60
ccggaaactc ggatctggcc acctctcccc ttggaagatc tcccagcaat ctagtttccc     120
ctctcggcgc cggggctccg gcagcgagga gcttaatctg cctctgagac tgcggctgtg     180
attttcgcct ttccacagaa gatctgcagt ctgcagagag ctgcccactc tgcacgcctg     240
tgtggaggga gagattggaa gcagtaccaa gcatggggaa cgaggggaag ttcgccttcg     300
ttgctccgta ggaagaccat ttccgtgtct ccatctctgt ccttccatat tcccctcgcg     360
```

```
ctgtcctccc tcttcagcct gcctgtccat ctctccatct gtctgttcaa gactgtgtcc    420
acatcaagcc gcatcccag cagctgcagt tttgctagag ccgggaaaga aacttaagga     480
tgcttacatt tccactgtgg aacgaattct gagcgccggg gagagcaggg cagcgcacaa    540
ccaatagcca cctgtctgtc ccgcccggga gcctcgcagg ctggagggcg gctggagagc    600
ggcggcggcc ggcggcgacg tgggcgccgt gggtcgggaa tccggcagtg cccaccaacc    660
gctgcgcccc gggaccgcca gcatgagcaa gcccgccgga tcaacaagcc gcattttaga   720
tatcccttgc aaagtgtgtg gtgaccgcag ctccgggaag cactacgggg tctacgcttg    780
cgacggctgc tccggattct tcaagaggag cattcgaagg aataggacct atgtctgcaa    840
gtctggaaac cagggaggat gccccgtaga caagacacac agaaaccaat gcagggcgtg    900
tcgactgaag aagtgtttgg aagtcaacat gaacaaagat gccgtgcagc acgagcgggg    960
tcctcggacg tccaccatcc gcaaacaggt ggctctctac ttccgtggac acaaggaaga   1020
caatggggcc gctgcgcact tcccctccac ggcgctgcca gcccctgctt tcttcacagc   1080
ggtcacgcag ctggagccgc acggtctgga gttggccgct gtgtctgcca ctcctgaacg   1140
gcagactctc gtgagcctgg ctcagcccac gcccaagtat ccccatgaag tgaatgggac   1200
cccaatgtat ctctacgaag tggccactga gtccgtgtgt gaatcagctg ccaggcttct   1260
ctttatgagc atcaagtggg caaagagtgt gccagccttt tccactttgt ctttacaaga   1320
tcagctgatg cttttggaag acgcgtggag agaactgttt gttctaggaa tagcacaatg   1380
ggccattccg gttgatgcta acactctact ggctgtatct ggcatgaata ctgacaacac   1440
agactcccag aagctgaaca agatcatatc tgaaatacag gctttgcaag aggtggtggc   1500
tcggttcaga cagctccgat tagacgccac tgaatttgcc tgtctgaaat gtattgtcac   1560
tttcaaagct gttcctacac acagtggttc tgaactgaga agtttccgga atgctgccgc   1620
cattgccgct ctccaagatg aggctcagct aactctcaac agctacattc ataccagata   1680
ccccacccaa ccctgccgat cgggaaaact cctgttgctt ttaccagctt tacggtcaat   1740
tagcccatct accatagaag aagtgttttt caaaaaaacc atcggcaatg tgccgattac   1800
aagactactt tcagatatgt acaaatccag tgacatctaa gggctccagt acccactttt   1860
ccaagatggg gcagtattag atggacatct acatgcaggt caagcctcaa aaaaaaagac   1920
tttctggaag gaaaaacttg ggagggagtg gccttcagga aaaaaaaaat gccaacggac   1980
tcaaaacaac agctatgacc tgctgtcccc ctgaaacagg acagctggaa aggccaggtg   2040
gttacaacag ttactgtcgc catgcccctgg gatgggtga actgggctca ccagcacagg   2100
ctgagccagg ttctgcctct gacctggaag atcccgctga atcattcaaa gctgaaagac   2160
aagccatgct ttcttctcct tcgtagcaca taaagtcagt tgatcaacag tagctttta   2220
tgtgacacca tcatatactg cagccttcag aactcgattg ggttggaaca tttacttaaa   2280
aaataatgct taggttttaa atcaaaagta ttatcaaaca ttttccttct atcataatac   2340
ttcattaagt ggccttcaga accaagcgag taagcgaaac gtagcttatg ctgtgtgatt   2400
tcctttccct cctcctcctc ctcctcccct ttctgttttt ttttcttttc ttttttctc    2460
tcttctcttc tcttctcttc tcttctcttc tcttctcttc tcttctctct tctctcttct   2520
ctcttctctc ttctctcttt cttctctctt tctctcttctc ataccgtagg tcaggcaacc  2580
tcgttaaagg aactgaggac aatggcactt ctccgcaaga cttcagggtg agcgcagcgg   2640
tggtgagaca caacagctct actgagaacc tccgtccaag gaggaggagt ccagacagca   2700
aaaccaaatg acgtggaacc aggtgattgg gtgaggtggt cgctgtcccg tcatcaaagt   2760
```

-continued

```
gctgaaaccaaaggccatagggtcagcgagtcacaccagacagtgaacaggagggacac    2820 aagccagaaagaacttcaaggagatgcgtgctaaacagatcctgaacgttccattgcta    2880 acagcctgagactcttggatgcctttcagaaaactctggtttctaataaagcctcaaatg    2940 catacatacacctcccccccaccccgtaccccccaccccacacaccatcctatactctca    3000 agctgctccttgggtatgaatctatacttatggaaatatagaaacaaacagttttaaata    3060 gctgctgtacttttcacgttttgatttattaggtactagcccgagggggaaattcagca    3120 ctggcttagcataggatgagtcaaacttctcttgtacaaagtgaattaactgatttgtga    3180 agttaaaaggttgtactcattgtatttacaaagaataaaaatatattgaatt    3232
```

<210> SEQ ID NO 2
<211> LENGTH: 385
<212> TYPE: PRT
<213> ORGANISM: Homo sapiens

<400> SEQUENCE: 2

```
Met Ser Lys Pro Ala Gly Ser Thr Ser Arg Ile Leu Asp Ile Pro Cys
  1               5                  10                  15

Lys Val Cys Gly Asp Arg Ser Ser Gly Lys His Tyr Gly Val Tyr Ala
             20                  25                  30

Cys Asp Gly Cys Ser Gly Phe Phe Lys Arg Ser Ile Arg Arg Asn Arg
         35                  40                  45

Thr Tyr Val Cys Lys Ser Gly Asn Gln Gly Gly Cys Pro Val Asp Lys
     50                  55                  60

Thr His Arg Asn Gln Cys Arg Ala Cys Arg Leu Lys Lys Cys Leu Glu
 65                  70                  75                  80

Val Asn Met Asn Lys Asp Ala Val Gln His Glu Arg Gly Pro Arg Thr
                 85                  90                  95

Ser Thr Ile Arg Lys Gln Val Ala Leu Tyr Phe Arg Gly His Lys Glu
            100                 105                 110

Asp Asn Gly Ala Ala Ala His Phe Pro Ser Thr Ala Leu Pro Ala Pro
        115                 120                 125

Ala Phe Phe Thr Ala Val Thr Gln Leu Glu Pro His Gly Leu Glu Leu
    130                 135                 140

Ala Ala Val Ser Ala Thr Pro Glu Arg Gln Thr Leu Val Ser Leu Ala
145                 150                 155                 160

Gln Pro Thr Pro Lys Tyr Pro His Glu Val Asn Gly Thr Pro Met Tyr
                165                 170                 175

Leu Tyr Glu Val Ala Thr Glu Ser Val Cys Glu Ser Ala Ala Arg Leu
            180                 185                 190

Leu Phe Met Ser Ile Lys Trp Ala Lys Ser Val Pro Ala Phe Ser Thr
        195                 200                 205

Leu Ser Leu Gln Asp Gln Leu Met Leu Leu Glu Asp Ala Trp Arg Glu
    210                 215                 220

Leu Phe Val Leu Gly Ile Ala Gln Trp Ala Ile Pro Val Asp Ala Asn
225                 230                 235                 240

Thr Leu Leu Ala Val Ser Gly Met Asn Thr Asp Asn Thr Asp Ser Gln
                245                 250                 255

Lys Leu Asn Lys Ile Ile Ser Glu Ile Gln Ala Leu Gln Glu Val Val
            260                 265                 270

Ala Arg Phe Arg Gln Leu Arg Leu Asp Ala Thr Glu Phe Ala Cys Leu
        275                 280                 285

Lys Cys Ile Val Thr Phe Lys Ala Val Pro Thr His Ser Gly Ser Glu
    290                 295                 300
```

-continued

```
Leu Arg Ser Phe Arg Asn Ala Ala Ile Ala Ala Leu Gln Asp Glu
305                 310                 315                 320

Ala Gln Leu Thr Leu Asn Ser Tyr Ile His Thr Arg Tyr Pro Thr Gln
            325                 330                 335

Pro Cys Arg Phe Gly Lys Leu Leu Leu Leu Pro Ala Leu Arg Ser
        340                 345                 350

Ile Ser Pro Ser Thr Ile Glu Glu Val Phe Phe Lys Lys Thr Ile Gly
        355                 360                 365

Asn Val Pro Ile Thr Arg Leu Leu Ser Asp Met Tyr Lys Ser Ser Asp
    370                 375                 380

Ile
385

<210> SEQ ID NO 3
<211> LENGTH: 25
<212> TYPE: DNA
<213> ORGANISM: artificial
<220> FEATURE:
<223> OTHER INFORMATION: RNAi target sequence

<400> SEQUENCE: 3
ggctgaagaa gtgtttggaa gtcaa                                         25

<210> SEQ ID NO 4
<211> LENGTH: 25
<212> TYPE: DNA
<213> ORGANISM: artificial
<220> FEATURE:
<223> OTHER INFORMATION: RNAi target sequence

<400> SEQUENCE: 4
ggagagaact gtttgttcta ggaat                                         25

<210> SEQ ID NO 5
<211> LENGTH: 25
<212> TYPE: DNA
<213> ORGANISM: artificial
<220> FEATURE:
<223> OTHER INFORMATION: RNAi target sequence

<400> SEQUENCE: 5
cattccggtt gatgctaaca ctcta                                         25

<210> SEQ ID NO 6
<211> LENGTH: 25
<212> TYPE: DNA
<213> ORGANISM: artificial
<220> FEATURE:
<223> OTHER INFORMATION: RNAi target sequence

<400> SEQUENCE: 6
cagattccca gaagctgaac aagat                                         25
```

MEANS AND METHODS FOR TREATING OR PREVENTING BRAIN TUMORS BASED ON THE NUCLEAR RECEPTOR TAILLESS (TLX)

This application is a National Stage of International Application No. PCT/EP2008/065731, filed Nov. 18, 2008, which is based upon and claims the benefit of priority from prior European Patent Application No. 07121641.0, filed Nov. 27, 2007, the entire contents of all of which are incorporated herein by reference in their entirety.

The present invention is concerned with therapeutic measures for brain tumors. Specifically, the present invention relates to the use of an inhibitor of tailless gene expression or tailless protein activity for the preparation of a pharmaceutical composition for treating or preventing the brain tumor in a subject. Preferably an inhibitor of tailless expression is a single or double stranded RNA. An inhibitor of tailless protein activity is preferably, an antibody which specifically binds thereto. Finally, the invention includes methods for identifying anti-brain tumor drugs.

The existence of a cancer stem cell population in human brain tumors of different pheno-types from both, children and adults, has been described (Vescovi 2006, Nat Rev Cancer 6: 425-436). However, the cellular origin of brain tumors remains a subject of an ongoing debate in the scientific literature. The decisive issue is whether brain tumors arise from the dedifferentiation of a normal brain cell or from the transformation of a normal neural stem cell or progenitor cell.

The tailless (Tlx) gene encodes an orphan nuclear receptor which is expressed in the developing eye and brain and in adult neural stem/progenitor cells. Tailless expressing cells also express CD 133, a widely used marker of brain tumor stem cells. Loss of tailless leads to a regulation of PTEN in the subventricular zone compatible with its function in control of neural stem cell proliferation. A series of studies showed that tailless is significantly overexpressed in human brain tumors. The tumor types included neurocytoma, glioma and ependymoma (Modena 2006, J Clin Oncol 24: 5223-5233; Phillips 2006, Cancer Cell 9: 157-173; Sharma 2007, Cancer Research 67: 890-900; Sim 2006, J Neuroscie 26: 12544-12555; Taylor 2005, Cancer Cell 8: 323-335).

Efficient and reliable therapies and therapeutic approaches for the treatment of brain tumors including neurocytoma, glioma and ependymoma as well as astrocytoma are not yet available but nevertheless highly desirable.

The technical problem underlying the present invention is to provide means and methods complying with those needs. The technical problem is solved by the embodiments characterized in the claims and herein below.

Accordingly, the present invention relates to the use of an inhibitor of tailless gene expression for the preparation of a pharmaceutical composition for treating or preventing a brain tumor in a subject.

The term "inhibitor of tailless gene expression" relates to a compound capable of inhibiting the formation (i.e. transcription) of RNA encoding the tailless nuclear receptor protein or to a compound which is capable of reducing the amount of such RNA present in a cell. Preferably, the inhibitor abolishes the de novo formation or the amount of tailless encoding RNA to an extent that the amount of tailless nuclear receptor protein in a cell which has been brought into contact the said inhibitor is significantly reduced compared to a cell which has not been contacted with the said inhibitor. Preferably, the compound suitable as an inhibitor of tailless gene expression is capable of interacting with a polynucleotide encoding the tailless nuclear receptor protein.

Polynucleotides encoding the tailless protein as referred to in accordance with the present invention are, preferably RNA molecules, more preferably mRNA molecules or precursors thereof. Also encompassed is, however, the genomic DNA of the tailless gene present in a cell. The aforementioned polynucleotides are, preferably, human polynucleotides. More preferably, the polynucleotide comprises a nucleic acid sequence as shown in SEQ ID NO: 1 or is a polynucleotide comprising a nucleic acid sequence encoding an amino acid sequence as shown in SEQ ID NO: 2. It is to be understood that the present invention also includes inhibitors of variants of the human tailless polynucleotides specifically referred to before. Variants are, preferably, polynucleotides comprising a nucleic acid sequence which is at least 70%, at least 80%, at least 85%, at least 90%, at least 95%, at least 97%, at least 98% or at least 99% identical to the nucleic acid sequence shown in SEQ ID NO: 1 or nucleic acid sequences encoding an amino acid sequence as shown in SEQ ID NO: 2. It is to be understood that the variant polynucleotides must encode a nuclear receptor having tailless function. Such polynucleotide variants, in particular, are represented by orthologs or paralogs of the tailless gene. The degree of sequence identity (in percentage values) as referred to above can be, preferably, determined by sequence comparison algorithms well known in the art and, in particular, by the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

Preferably, inhibitors of tailless gene expression are single or double stranded RNA molecules which are capable of specifically binding to a tailless polynucleotide referred to above. Such single or double stranded RNA molecules are used for gene expression regulation by means of antisense RNA or ribozyme technology or RNA interference (RNAi) technology). Other preferred inhibitors of tailless gene expression are triple helix forming oligonucleotides, preferably DNA oligonucleotides. The molecular principles of the aforementioned technologies are well known in the art.

RNAi is mediated by small interfering RNAs (siRNAs). The term "small interfering RNA" or "siRNA" refers to a nucleic acid molecule which is a double stranded RNA agent that is complementary to i.e., able to base-pair with, a portion of a target RNA (generally mRNA), i.e. the polynucleotide of the present invention being RNA. siRNA acts to specifically guide enzymes in the host cell to cleave the target RNA. By virtue of the specificity of the siRNA sequence and its homology to the RNA target, siRNA is able to cause cleavage of the target RNA strand, thereby inactivating the target RNA molecule. Preferably, the siRNA which is sufficient to mediate RNAi comprises a nucleic acid sequence comprising an inverted repeat fragment of the target gene and the coding region of the gene of interest (or portion thereof). Also preferably, a nucleic acid sequence encoding a siRNA comprising a sequence sufficiently complementary to a target gene is operatively linked to a expression control sequence. Thus, the mediation of RNAi to inhibit expression of the target gene can be modulated by said expression control sequence. Preferred expression control sequences are those which can be regulated by a exogenous stimulus, such as the tet operator whose activity can be regulated by tetracycline or heat inducible promoters. Alternatively, an expression control sequence may be used which allows tissue-specific expression of the siRNA. The complementary regions of the siRNA allow sufficient hybridization of the siRNA to the target RNA and thus mediate RNAi. In mammalian cells, siRNAs are approximately 21-25 nucleotides in length. The siRNA sequence needs to be of sufficient length to bring the siRNA and target RNA together through complementary base-pairing interactions. The siRNA used with the Tet expression system of the invention may be of varying lengths. The length of the siRNA is preferably greater than or equal to ten nucleotides and of sufficient length to stably interact with the target RNA; specifically 15-30 nucleotides; more specifically any integer between 15 and 30 nucleotides, most preferably 15, 16, 17, 18, 19, 20, 21, 22, 23, 24, 25, 26, 27, 28, 29, and 30. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target under physiological conditions). Generally, such complementarity is 100% between the siRNA and the RNA target, but can be less if desired, preferably 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. When selecting between allelic targets, choice of length is also an important factor because it is the other factor involved in the percent complementary and the ability to differentiate between allelic differences. Methods relating to the use of RNAi to silence genes in organisms, including *C. elegans*, *Drosophila*, plants, and mammals, are known in the art (see, for example, Fire et al., Nature (1998) 391:806-811; Fire, Trends Genet. 15, 358-363 (1999); WO 0129058; WO 09932619).

The ribozyme- and antisense-based techniques for gene silencing are well known in the art (see Kalota 2004, Cancer Biology & Therapy 3:1 4-12). They are essentially based on antisense nucleic acid molecules or ribozymes which comprise nucleic acid sequences which are complementary to the target polynucleotides and, thereby, allow for specific binding to the target polynucleotides. As a consequence of said specific binding, the target polynucleotides will than be degraded or inactivated. Oligonucleotides as used herein, preferably, relate to small double stranded DNA molecules which are either capable of binding to specific regions of a target genomic DNA whereby gene silencing is achieved (so-called triple helix forming oligonucleotides) or to oligonucleotides which act as decoys to sequester transcription factor specifically required for the transcription of a target gene These techniques have also been successfully used in vivo and also to some extend resulted already in therapeutics. (see also Kalota 2004 loc cit.). More preferably the inhibitor of tailless expression is a single or double stranded RNA or an oligonucleotide which specifically binds to a polynucleotide comprising a nucleic acid sequence selected from the group consisting of:

a) a nucleic acid sequence as shown in SEQ ID NO: 1;
b) a nucleic acid sequence encoding an amino acid sequence as shown in SEQ ID NO: 2; and
c) a nucleic acid sequence which is at least 70%, at least 80%, at least 85%, at least 90%, at least 95%, at least 97%, at least 98% or at least 99% identical to the nucleic acid sequence of i) or ii) wherein that nucleic acid sequence encodes a tailess polypeptide.

More preferably, the inhibitor of tailess expression is a single or double stranded RNA comprising or essentially consisting of a nucleic acid having a nucleotide sequence as shown in any one of SEQ ID NOs: 3 to 6.

The term "pharmaceutical composition" as used herein comprises the compounds of the present invention (i.e. inhibitors of tailess gene expression/protein function) and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, nucleic acid compounds may be administered in a gene therapy approach by using viral vectors or viruses or liposomes. Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. The pharmaceutical compositions and formulations referred to herein are administered at least once in order to treat or ameliorate or prevent brain tumors as recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "treating" means that the brain tumors or symptoms thereof referred to in accordance with the present invention are at least ameliorated or, more preferably, even entirely removed in a statistically significant portion of subjects to which a compound suitable as a inhibitor of tailless gene expression or protein function has been administered. Whether a portion is statistically significant can be determined without further ado by the person skilled in the art using various well known statistic evaluation tools, e.g., determination of confidence intervals, p-value determination, Student's t-test, Mann-Whitney test, etc. Preferred confidence intervals are at least 90%, at least 95%, at least 97%, at least 98% or at least 99%. The p-values are, preferably, 0.1, 0.05, 0.01, 0.005, or 0.0001.

The term "preventing" as used herein means that the de novo formation of brain tumors can be abolished in a statistically significant portion of subjects to which the compounds suitable as a inhibitor of tailless gene expression or protein function have been administered.

The term "brain tumor" relates to a tumor which arises from tissues of the nervous system and, preferably, of the central system. More preferably, a brain tumor in accordance with the present invention is a glioma, neurocytoma, astrocytoma or ependymoma. Most preferably, the tumor arises from CD133 positive cancer stem cells.

The term "subject" as used herein preferably relates to mammals and most preferably to humans.

It has been found in accordance with the studies underlying the present invention that the orphan nuclear receptor tailless has oncogenic potential rather than being merely a marker for brain tumors. Moreover, it was found that inhibiting tailless function in adult neural stem cells or brain tumor cells by interfering with the tailless gene expression or the tailless nuclear receptor protein function will lead to treatment or prevention of brain tumors including glioma, neurocytoma, astrocytoma or ependymoma. Specifically, transgenic mice expressing two copies of the tailless gene were generated in accordance with studies underlying this invention. These mice developed brain tumors from adult neuronal stem cells. The observed brain tumors included glioma-like structures and other tumors referred to in accordance with the present invention. As discussed above already, tailless was also found to be upregulated in gene expression profiles of various brain tumors (Modena 2006, loc cit; Phillips 2006, loc cit., Sharma 2007, loc cit, Sim 2006, loc cit., Taylor 2005 loc cit.). Specifically, a recent study showed that 50% of the analyzed glioblastomas exhibited tailless overexpression on the mRNA level. Contrary, mice lacking tailless in adult neuronal stem cells due to a conditional knock out of the tailless gene in the adult brain also showed significantly reduced neurogenesis. These data show that tailless, indeed, is a molecular regulator of neurogenesis in the adult brain including impaired neurogenesis which occurs in brain tumor formation. Moreover, thanks to the means and methods provided in accordance with the present invention, tailless can be addressed as a molecular target for brain cancer therapies. Moreover, it has been found that the therapeutic means and measures referred to herein will be also effective against brain tumors which are derived from CD133 positive cancer stem cells. Such tumors are normally not affected by conventional tumor therapies such as chemotherapy or irradiation.

From the above it is to be understood that the present invention also contemplates the use of an inhibitor of tailless protein activity for the preparation of a pharmaceutical composition for treating or preventing a brain tumor.

The term "inhibitor of tailless protein activity" encompasses compounds which interfere with the tailless protein activity. Preferably, such compounds specifically bind to the tailless nuclear receptor protein thereby inhibiting its capability to bind to its natural binding partners. In this context, the tailless protein is known to form homo- or heterodimers with of the nuclear receptor proteins to exert its biological functions. Such homo- or heterodimerization can be prevented by antibodies specifically binding to a tailless nuclear receptor protein or by dominant negative nuclear receptor proteins known to interact with tailless protein including tailless itself (see Zhu 1996, Endocrinology 137(2): 712-721).

More preferably, the inhibitor is an antibody which specifically binds to a protein encoded by a polynucleotide having a nucleic acid sequence selected from the group consisting of:
  a) a nucleic acid sequence as shown in SEQ ID NO: 1;
  b) a nucleic acid sequence encoding a polypeptide having an amino acid sequence as shown in SEQ ID NO: 2; and
  c) a nucleic acid sequence being at least 70% identical to the nucleic acid sequence of a) or b) wherein said sequence encodes a tailless protein.

Antibodies against the tailless protein according to the invention can be prepared by well known methods using a purified tailless protein or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the term "antibody" as used in accordance with the present invention is a monoclonal antibody, a polyclonal antibody, a single chain antibody, a human or humanized antibody or primatized, chimerized or fragment thereof. Also comprised by the term "antibodies" are a bispecific antibody, a synthetic antibody, an antibody fragment, such as Fab, Fv or scFv fragments etc., or a chemically modified derivative of any of these. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals. The said antibody shall specifically bind (i.e. does not cross react with other polypeptides or peptides) to the tailless protein. Specific binding can be tested by various well known techniques. Moreover, the antibodies useful as compounds capable of inhibiting tailless protein function can be tested for this property in functional assays such as nuclear localization assays. An antibody shall be capable of inhibiting tailless protein function if it prevents nuclear localization. Moreover, dimerization can be analyzed. An antibody shall be capable of inhibiting tailless protein function if it prevents homo- or heterodimerization of the tailless protein.

The present invention finally also contemplates a method for treating or preventing brain tumors in a subject comprising administering to a subject suffering from a brain tumor an inhibitor of tailless gene expression or an inhibitor of tailless protein activity in a therapeutically effective amount. Preferred embodiments of the said method have been discussed in connection with the uses of the present invention above.

Moreover, the present invention contemplates a method for identifying an anti-brain tumor drug comprising:
(a) contacting a host cell expressing the tailless gene with a compound suspected to be a candidate anti-brain tumor drug;
(b) determining the amount of tailless protein in said host cell; and
(c) comparing the amount of tailless protein found in the said host cell to the amount of tailless found in a reference host cell which has not been brought into contact with the said compound suspected to be a candidate anti-tumor drug wherein a decreased amount of tailless protein found in the host cell compared to the reference host cell is indicative for a compound being a candidate anti-brain tumor drug.

Further, the present invention includes a method for identifying an anti-brain tumor drug comprising:
(a) contacting a host cell comprising the tailless protein with a compound suspected to be a candidate anti-brain tumor drug;
(b) determining the biological activity of the tailless protein in said host cell; and
(c) comparing the biological activity of tailless protein found in the said host cell to the biological activity of the tailless protein found in a reference host cell which has not been brought into contact with the said compound suspected to be a candidate anti-tumor drug, wherein a decreased activity found in the host cell compared to the reference host cell is indicative for a compound being a candidate anti-brain tumor drug.

The expression "a compound suspected to be a candidate anti-brain tumor drug" are in accordance with the aforementioned method, preferably, compounds including small molecule compounds which are capable of specifically interfering with the transcription or translation of the tailless gene. Preferred compounds are the single or double stranded RNA molecules or oligonucleotides referred to elsewhere in this specification. Further compounds are those which interfere with the biological activity of the tailless protein. Preferred compounds in such a context are small molecules or the antibodies and tailless mutant proteins referred to elsewhere in this specification. Depending on the chemical nature of the compounds, the said compounds may be diluted in the medium comprising the host cells or may be delivered by known vehicles such as liposomes and the like. By "contacting" it is meant that the host cell is brought into physical contact for a time period sufficient for allowing interaction of the tailless polynucleotide transcripts or the tailless polypeptides present in the said host cell.

The term "host cell" as used herein refers to a host cell which is capable of expressing the tailless gene, i.e. a host cell which allows for transcription of the tailless gene into a tailless encoding mRNA and the translation of the said mRNA into the tailless protein. Preferably, the term relates to a eukaryotic host cell, more preferably to a mammalian host cell and, most preferably, to a human host cell. It is to be understood that tailless gene expression includes either naturally occurring tailless gene expression which can be found in brain cells and, in particular, in adult neuronal stem cells or brain tumor cells including those specifically mentioned herein or heterologous expression of the tailless gene, e.g., transient expression from an expression vector comprising the tailless gene or cDNA or expression from a transgene which has been stably integrated into the host cell genome.

The amount of tailless protein can be determined by various techniques for protein detection known in the art. These techniques include the detection of the amount of the tailless protein by antibodies specifically recognizing the tailless protein or chromatographic methods. Also encompassed are, however, methods which aim to determine the amount of tailless protein by measuring specific physico-chemical parameters of the said protein, such as NMR—or mass spectrometry (MS)—based techniques. The amount of tailless protein can, of course, also be determined indirectly, i.e. by measuring its biological activity. The amount, thus, determined will be compared to the amount of tailless protein determined by the same technique in a reference host cell. The comparison may be carried out manually or computer-assisted. A decrease in the amount or activity in the treated host cell (i.e. the host cell which has been contacted to the putative drug) will be indicative for a compound which is capable of interfering with tailless gene expression or the tailless biological activity and, thus, a compound suitable as a candidate anti-brain tumor drug.

All references refer to above are herewith incorporated by reference with respect to their entire disclosure content as well as their specific disclosure content explicitly referred to in the above description.

The figures show:

FIG. 1: Neurogenesis in the adult SVZ is Tlx dosage dependent; Mice with different copy number of the Tlx gene show that neurogenesis in the adult SVZ is Tlx dosage-dependent.

Figure 2:
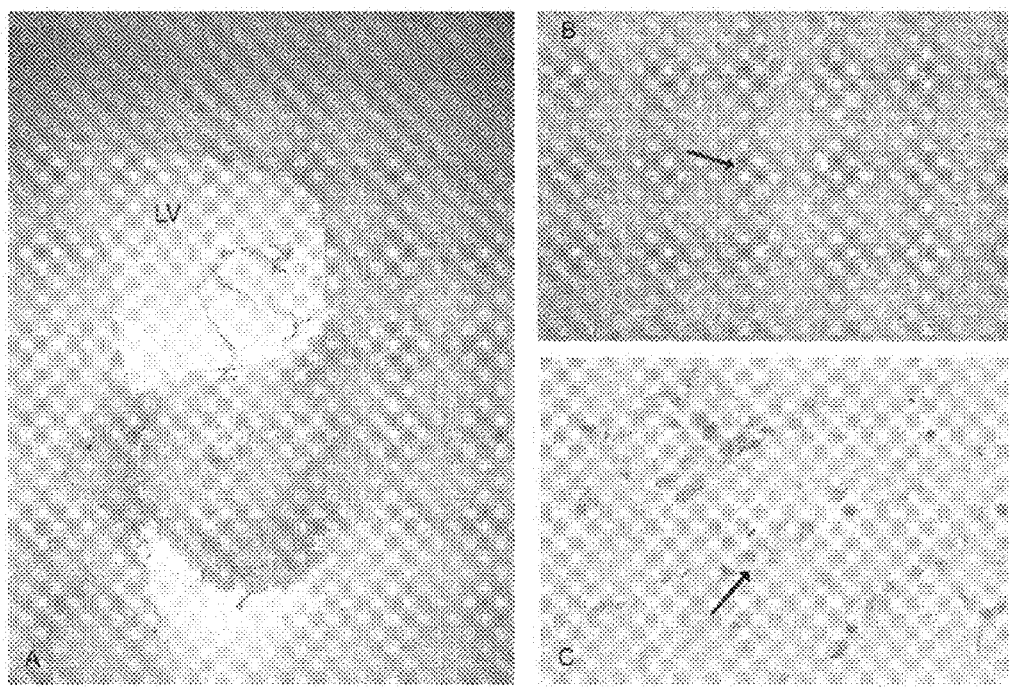

FIG. 2: Overexpression of Tlx leads to Brain tumor formation; (A) Development of brain tumors in the SVZ of Tlx overexpressing mice; (B) Tumor cells are migrating along white matter tracts (arrow); (C) Tumor cells surround neurons.

The invention will now be illustrated by the following examples which are not intended to restrict or limit the scope of this invention.

EXAMPLE 1

Analysis of Tlx Overexpressing Mice

To mimic overexpression of Tlx in human brain tumors, a transgenic mouse overexpressing Tlx was generated. A bacterial artificial chromosome (BAC)-based technology was applied, which means that the overexpression of Tlx is derived by the endogenous Tlx regulatory sequences. These led to specific overexpression of Tlx in neural stem cells in which the endogenous gene is expressed. Tlx-overexpressing mice with increasing copy number of the transgene show that neurogenesis in the adult is Tlx dosage-dependent (FIG. 1). The increased neurogenesis in Tlx overexpressing mice indicates that Tlx can promote self-renewal of adult neural stem cell.

Interestingly, the 2 copy Tlx transgenic line starts to develop brain tumors when they are about 1 year old (FIG. 2 A) with characteristics of human brain tumors. The tumor cells are migrating along the white matter tracts (FIG. 2 B) and they surround neurons (FIG. 2 C). The mice also develop glioma-like lesions. These glioma-like structures express GFAP and DCX which are characteristics of human glioma cells. The cell density in these structures is much higher than in normal brain tissue and they express the cell proliferation marker Ki67, which indicates that these cells are highly proliferating.

Since Tlx was overexpressed only in neural stem cells, brain tumor formation in the Tlx overexpressing line indicates that this brain tumor is a stem cell disease. This is the first mouse model which directly proves that a brain tumor arises from a mutated stem cell population.

To determine whether self-renewal of adult neural stem cells depends on Tlx expression, an inducible Tlx knock-out mouse was analyzed by crossing the Tlx-CreERT2 mice with the mice in which the Tlx gene is floxed. Two weeks after induction of recombination in the adult mouse brain, neurogenesis in the SVZ is dramatically decreased as indicated by BrdU pulse labeling and DCX staining (FIG. 4 A, B). Four weeks after induction there is basically no cell division in the SVZ suggesting that adult neurogenesis in the SVZ depends on Tlx expression (FIG. 4 C). Taken together with the Tlx expression pattern, it was concluded that expression of Tlx is required for the self-renewal of adult neural stem cells.

In summary, it was shown that the nuclear receptor Tailless is playing a central and decisive role in regulating self-renewal of adult neural stem cells. Tlx overexpression stimulates brain tumor formation from adult neural stem cells. These findings allow for a direct targeting of brain tumor stem cells by interfering with Tlx function. It is also possible to detect the initiating stages of brain tumor formation by analyzing Tlx expression.

EXAMPLE 2

Inhibitors of Tailless Gene Expression

The following Oligonucleotides can be used to knock down the tailless gene expression:

| SEQ ID No: | start | Sequence (DNA) | Region | GC% |
|---|---|---|---|---|
| 3 | 389 | GGCTGAAGAAGTGTTTGGAAGTCAA | ORF | 44.0 |
| 4 | 833 | GGAGAGAACTGTTTGTTCTAGGAAT | ORF | 40.0 |
| 5 | 870 | CATTCCGGTTGATGCTAACACTCTA | ORF | 44.0 |
| 6 | 926 | CAGATTCCCAGAAGCTGAACAAGAT | ORF | 44.0 |

"Start" indicates the nucleotide position with respect to the cDNA sequence of human tailless.

The oligonucleotides will be chemically synthesized as double stranded oligonucleotides or siRNA. The oligonucleotides or siRNA molecules will be formulated in a pharmaceutical acceptable manner and can be introduced into brain tumor tissue as described in, e.g., Kalota loc. cit. Upon uptake of the oligonucleotides or siRNA molecules, the brain tumor cells will stop expressing tailless. As a consequence thereof, the brain tumor will retard as can be monitored by clinical diagnostic techniques such as PET.

The invention claimed is:

1. A method for treating or preventing a brain tumor in a subject comprising administering in a therapeutically effective amount an inhibitor of tailless gene expression, said inhibitor being a single or double stranded RNA which specifically binds to a polynucleotide having a nucleic acid sequence selected from the group consisting of:

a) a nucleic acid sequence as shown in SEQ ID NO: 1;

b) a nucleic acid sequence encoding a polypeptide having an amino acid sequence as shown in SEQ ID NO: 2; and c) a nucleic acid sequence being at least 70% identical to the nucleic acid sequence of a) or b) wherein said sequence encodes a tailless protein.

2. The method of claim 1, wherein said inhibitor of tailless expression is a single or double stranded RNA comprising or essentially consisting of a nucleic acid having a nucleotide sequence as shown in any one of SEQ ID NOs: 3 to 6.

3. The method of claim 1, wherein said brain tumor is a glioma, astrocytoma, neurocytoma or ependymoma.

4. The method of claim 1, wherein said subject is a human.

* * * * *